United States Patent [19]

Schulte-Elte et al.

[11] 4,369,328
[45] Jan. 18, 1983

[54] OXYGENATED ALICYCLIC COMPOUNDS AND PROCESS FOR PREPARING SAME

[75] Inventors: Karl-Heinrich Schulte-Elte, Onex; Bernard Egger, Bernex; Bernard Muller, Geneva, all of Switzerland

[73] Assignee: Firmenich SA, Geneva, Switzerland

[21] Appl. No.: 286,689

[22] Filed: Jul. 24, 1981

[30] Foreign Application Priority Data

Aug. 26, 1980 [CH] Switzerland .................... 6413/80

[51] Int. Cl.$^3$ .......................................... C07D 303/48
[52] U.S. Cl. .................................. 549/546; 568/377; 568/378; 560/128; 562/510
[58] Field of Search .................. 260/348.55; 549/546

[56] References Cited

U.S. PATENT DOCUMENTS

| | | | |
|---|---|---|---|
| 3,141,027 | 7/1964 | Phillips et al. | 260/348.55 |
| 3,892,809 | 7/1975 | Schulte-Elte | 260/348.55 |
| 3,931,326 | 1/1976 | Kovats et al. | 568/377 |

Primary Examiner—Norma S. Milestone
Attorney, Agent, or Firm—Scully, Scott, Murphy and Presser

[57] ABSTRACT

New oxygenated alicyclic compounds of formula

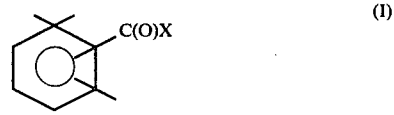

(X=OH, alkyl, O-alkyl) are useful as starting materials for the preparation of cyclohexadienic derivatives of formula

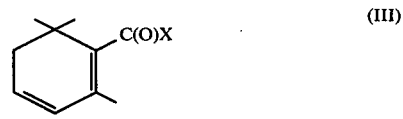

(X=OH, alkyl, O-alkyl). They are converted into compounds (III) by treating them with an acidic dehydrating agent in the presence of an inert organic solvent. Compounds (I) are manufactured by reacting compounds (II)

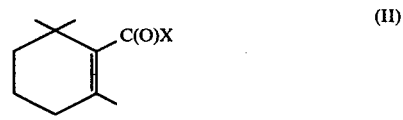

(X=OH, alkyl, O-alkyl) with an organic peracid.

3 Claims, No Drawings

OXYGENATED ALICYCLIC COMPOUNDS AND PROCESS FOR PREPARING SAME

BRIEF SUMMARY OF THE INVENTION

The instant invention relates to new oxygenated alicyclic compounds of formula (I)

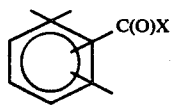

wherein X represents an OH or an O-alkyl group, or an alkyl radical.

The invention relates also to a process to prepare compounds (I), which process comprises reacting compounds (II)

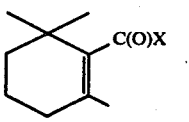

(X=OH, alkyl, O-alkyl), with an organic peracid.

The invention finally provides a process to prepare compounds (III)

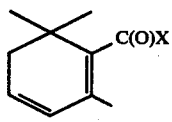

(X=OH, alkyl, O-alkyl), which comprises treating compounds (I) with an acidic dehydrating agent.

BACKGROUND OF THE INVENTION

Several publications describe the preparation of cyclohexadienic derivatives of the type of those of formula (III). For instance, the preparation of 2,6,6-trimethyl-cyclohexa-1,3-dien-1-yl methyl ketone [X=CH$_3$ in formula (III)] has been disclosed in Chem. Comm. 1973, 161. 2,6,6-Trimethyl-cyclohexa-1,3-dien-1-carboxylic acid, as well as the corresponding methyl and ethyl esters [X=OH, OCH$_3$ or OC$_2$H$_5$ in formula (III)], are prepared from the corresponding mono-unsaturated compound of formula (IV)

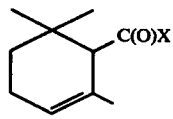

(X=OH, OCH$_3$, OC$_2$H$_5$), by reacting them with a halogen and subsequently dehydrohalogenating the obtained halo-derivative [see e.g. Compt. Rend. Ser. C, 262, 1725 (1966) and Helv. Chim. Acta 38, 1863 (1955)]. These methods however have not been developed for industrial scale preparations as they have been found uneconomical and difficult to scale-up. These disadvantages of the prior known syntheses have been overcome by the process of the present invention.

PREFERRED EMBODIMENTS OF THE INVENTION

In the above given definition, symbol X can represent an alkyl radical. Preferably this is a lower alkyl radical having from 1 to 3 carbon atoms, for example methyl, ethyl or n-propyl.

Preferred species of the compounds of formula (I) include the following:

2,6,6-trimethyl-1,2-epoxy-cyclohexane-1-carboxylic acid, methyl 2,6,6-trimethyl-1,2-epoxy-cyclohexane-1-carboxylate, ethyl 2,6,6-trimethyl-1,2-epoxy-cyclohexane-1-carboxylate, and 2,6,6-trimethyl-1,2-epoxy-cyclohexyl methyl ketone.

According to the invention, compounds (I) are obtained starting from the compounds of formula (II) by reacting them with an organic peracid, more particularly an organic peracid possessing a high epoxydizing power such as for example permaleic, m-chloro-perbenzoic, performic, perphthalic or mono-chloroperacetic acid. For practical and economical reasons, permaleic acid is preferred. The said reaction is effected in accordance with known techniques in the presence of an inert organic solvent, for instance a hydrocarbon such as toluene or a chlorinated hydrocarbon such as methylene chloride or trichloroethylene. The reaction temperature is generally kept at between about 0° and 50° C., more particularly at between about 30° and 40° C.

The mono-unsaturated compounds of formula (II), used as starting materials in the above disclosed process, are known chemical entities and they can be obtained according to described methods. For instance, one may cite the following:

X=OH: Compt. Rend. Sér. C, 262, 1725 (1966)

X=OCH$_3$: Chem. Abstr. 57, 1240 g (1962)

X=CH$_3$: Chem. Comm. 1973, 161.

In accordance with the present invention above defined compounds (I), when subjected to the action of an acidic dehydrating agent, can be converted into their corresponding cyclohexadienic derivatives of formula (III).

Suitable acidic dehydrating agents include strong mineral of organic acids such as phosphoric, perchloric, sulphuric and p-toluenesulphonic acid, or potassium hydrogeno-sulphate. For practical and economical reasons, acidic diatomaceous earth are used, preferably in suspension in an inert organic solvent such as an ether, e.g. dioxane, or a ketone such as acetone. The reaction of the epoxyde of formula (I) with the acidic dehydrating agent is preferably carried out at a temperature in the vicinity of the boiling point of the solvent or mixture of solvents chosen. In the course of the reaction, we observed the formation of a novel hydroxylated intermediate of formula (V)

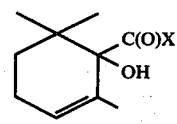

(X=OH, alkyl, O-alkyl), which compound could be isolated and identified whenever desired. However, this is optional and the reaction can in fact be carried out until complete conversion into end-products (III).

The invention is illustrated in a more detailed manner in the following examples wherein the temperatures are indicated in degrees centigrade.

EXAMPLE 1

Methyl 2,6,6-trimethyl-1,2-epoxy-cyclohexane-1-carboxylate 25.0 g (0.75 M) of 70% hydrogen peroxyde have been added under stirring to a mixture of 91.0 g (0.50 M) of methyl β-cyclogeraniate and 73.5 g (0.75 M) of maleic anhydride in 250 ml of $CH_2Cl_2$. The addition is effected dropwise at such a rate as to keep the temperature of the reaction mixture at between 30° and 38°. Stirring was kept until complete conversion of starting β-cyclogeraniate (5 h), whereupon the mixture was cooled and the formed maleic acid was filtered. The organic phase was successively washed with $H_2O$, an aqueous saturated $Na_2CO_3$ solution and $H_2O$ until neutrality. After drying over $Na_2SO_4$, concentration and distillation, there were collected 91.1 g (yield 92%) of the desired products, b.p. 45°/0.1 Torr:

IR: 1740 $cm^{-1}$;

NMR: 1.08 (3H, s); 1.14 (3H, s); 1.26 (3H, s); 3.77 (3H, s) δppm;

MS: $M^+$ = 198(2); m/e = 183(7), 166(8), 155(12), 142(53), 123(22), 115(49), 95(51), 85(35), 69(74), 55(64), 43(100), 41(65), 29(21).

EXAMPLE 2

Ethyl 2,6,6-trimethyl-1,2-epoxy-cyclohexane-1-carboxylate 98.0 g (0.5 M) of ethyl β-cyclogeraniate have been treated, as described in Example 1, with maleic anhydride and hydrogen peroxide to give the desired ester with a yield of 90%, b.p. 55°/0.1 Torr:

IR: 1735 $cm^{-1}$;

NMR: 1.06 (3H, s); 1.13 (3H, s); 1.23 (3H, s); 4.22 (2H, 2t) δppm;

MS: $M^+$ = 212(5); m/e = 197(3), 184(3), 166(9), 156(48), 139(24), 129(48), 111(34), 95(51), 87(40), 69(83), 55(65), 43(100), 41(60), 29(55).

EXAMPLE 3

2,6,6-Trimethyl-1,2-epoxy-cyclohexyl methyl ketone 8.3 g (0.05 M) of 2,6,6-trimethyl-cyclohex-1-enyl methyl ketone have been treated with maleic anhydride and hydrogen peroxide according to Example 1, to give, after extraction and purification as described above, 8.5 g (yield 95%) of the desired product, b.p. 85°/6 Torr:

IR: 1700 $cm^{-1}$;

NMR: 1.07 (3H, s); 1.13 (3H, s); 1.17 (3H, s); 2.20 (3H, s) δppm;

MS: $M^+$ = 182(0.5); m/e = 140(12), 125(45), 111(35), 96(14), 84(10), 69(70), 55(71), 43(100), 27(10).

EXAMPLE 4

2,6,6-Trimethyl-1,2-epoxy-cyclohexane-1-carboxylic acid 84.0 g (0.5 M) of β-cyclogeranic acid were treated, as indicated in Example 1, with 73.5 g (0.75 M) of maleic anhydride and 25.0 g (0.75 M) of 70% hydrogen peroxyde. After cooling, the reaction mixture was extracted with an aqueous 10% solution of NaOH and the aqueous extracts were neutralized with 10% $H_2SO_4$. On evaporation, there were collected 55.3 g (yield 60%) of the desired acid having a purity of 75% as indicated by thin-layer chromatography. An analytical sample showed the following data:

IR: 3300 and 1750 $cm^{-1}$;

NMR: 1.05 (3H, s); 1.26 (3H, s); 1.32 (3H, s) δppm;

MS: $M^+$ = 184(1).

EXAMPLE 5

Methyl 2,6,6-trimethyl-1,2-epoxy-cyclohexane-1-carboxylate 24.6 g (0.11 M) of m-chloroperbenzoic acid were added dropwise at 0° to a solution of 18.2 g (0.10 M) of methyl β-cyclogeraniate in 125 ml of $CH_2Cl_2$. Once the addition was over, stirring was maintained for 3 additional hours and the mixture was then kept standing at room temperature for 24 h.

After filtration, wasing over $Na_2SO_4$, concentration and distillation of the residue under reduced pressure (0.1 Torr), there were obtained 19.6 g (yield 84%) of the desired product.

EXAMPLE 6

Methyl 2,6,6-trimethyl-cyclohexa-1,3-diene-1-carboxylate 99.0 g (0.5 M) of methyl 2,6,6-trimethyl-1,2-epoxy-cyclohexane-1-carboxylate have been added to 50 g of acidic diatomaceous earth (preliminarily dried by azeotropic distillation with toluene) in suspension in 200 ml of dioxane. The stirred reaction mixture was heated at reflux (100°) under nitrogen for 4 h, then it was cooled and filtered over CELITE and concentrated. By distilling the residue, there were obtained 64.4 g (yield 65%) of the desired product, b.p. 52°/7 Torr. The thus obtained product was identical with a sample prepared according to Compt. Rend. Sér. C, 262, 1725 (1966).

In the course of the reaction, there was isolated and identified the compound of formula

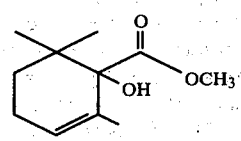

IR: 3500, 1730 $cm^{-1}$;

NMR: 0.83 (3H, s); 0.99 (3H, s); 1.59 (3H, m); 3.88 (3H, s); 5.66 (1H, m) δppm;

MS: $M^+$ = 198(2); m/e = 166(5), 138(33), 130(13), 121(7), 111(20), 95(47), 82(21), 70(49), 69(100), 55(32), 43(68), 27(11).

EXAMPLE 7

Ethyl 2,6,6-trimethyl-cyclohexa-1,3-diene-1-carboxylate 105 g (0.5 M) of 2,6,6-trimethyl-1,2-epoxy-cyclohexane-1-carboxylate have been treated with 50 g of acidic diatomaceous earth as indicated in Example 6 (4 h at 100°). The desired ester was obtained with a yield of 62%. The product thus obtained was identical to a sample prepared according to Helv. Chim. Acta 38, 1863 (1955).

In the course of the reaction, there was isolated and identified a compound of formula

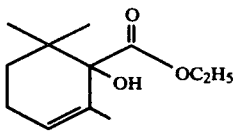

IR: 3500, 1720 cm$^{-1}$;

NMR: 0.83 (3H, s); 0.98 (3H, s); 1.3 (3H, t, J=3 Hz); 1.6 (3H, m); 2.08 (2H, m); 4.21 and 4.32 (2H, 2t, J=3 Hz); 5.63 (1H, m) δppm;

MS: M$^+$=212(1); m/e=139(77), 121(4), 95(42), 82(26), 55(6), 43(100), 29(7).

EXAMPLE 8

2,6,6-Trimethyl-cyclohexa-1,3-dien-1-yl methyl ketone 2.0 g (0.011 M) of 2,6,6-trimethyl-1,2-epoxy-cyclohexyl methyl ketone have been treated with 0.5 g of acidic diatomaceous earth in 10 ml of dioxane at 100° to give, after the usual treatments as described in Example 6, 1.3 g (yield 72%) of the desired product (purity 80%).

An analytical sample was found identical to the product prepared according to Chem. Comm. 1973, 161.

In the course of the reaction, there was also isolated and identified a compound of formula

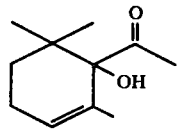

IR: 3450, 1700 cm$^{-1}$;

NMR: 0.8 (3H, s); 1.0 (3H, s); 1.5 (3H, m); 2.22 (3H, s); 4.1 (1H, broad s); 5.7 (1H, m) δppm;

MS: m/e=139(35), 95(30), 81(5), 67(5), 55(7), 43(100).

EXAMPLE 9

2,6,6-Trimethyl-cyclohexa-1,3-dien-1-carboxylic acid 12.2 g of 2,6,6-trimethyl-1,2-epoxy-cyclohexane-1-carboxylic acid (purity about 75%; see Example 4) were heated at 100° in the presence of 5 g of acidic diatomaceous earth and 50 ml of dioxane, until complete disappearance of the starting material (control by thin-layer chromatography). After having subjected the reaction mixture to the same treatments as described in Example 4, there were obtained 4.6 g of a mixture containing ca. 55% of the desired product as indicated by spectroscopy.

NMR: 1.18 (6H, 2s); 1.96 (3H, s); 2.14 (2H, d, J=3 Hz); 5.9 (1H, m); 8.7 (1H, broad m) δppm.

The desired acid can also be isolated and purified by esterification of the reaction mixture followed by preparative gas chromatography and saponification.

What we claim is:
1. 2,6,6-Trimethyl-1,2-epoxy-cyclohexane-1-carboxylic acid.
2. Methyl 2,6,6-trimethyl-1,2-epoxy-cyclohexane-1-carboxylate.
3. Ethyl 2,6,6-trimethyl-1,2-epoxy-cyclohexane-1-carboxylate.

* * * * *

UNITED STATES PATENT AND TRADEMARK OFFICE
CERTIFICATE OF CORRECTION

PATENT NO. : 4,369,328

DATED : January 18, 1983

INVENTOR(S) : Karl-Heinrich Schulte-Elte, et al.

It is certified that error appears in the above-identified patent and that said Letters Patent are hereby corrected as shown below:

ON THE TITLE PAGE, in the

ABSTRACT, first formula and column 1, line 10, the correct formula should read as -- 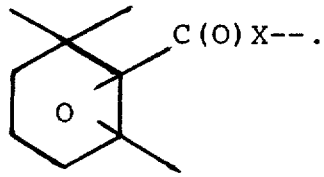 --.

Signed and Sealed this

Twenty-seventh Day of September 1983

[SEAL]

Attest:

GERALD J. MOSSINGHOFF

*Attesting Officer*    *Commissioner of Patents and Trademarks*